(12) United States Patent
Aoki et al.

(10) Patent No.: US 6,465,676 B2
(45) Date of Patent: Oct. 15, 2002

(54) AMINOPOLYCARBOXYLATES, PROCESS FOR PRODUCING THE SAME AND USE THEREOF

(75) Inventors: Masahiro Aoki; Yasushi Hara, both of Yamaguchi (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/760,663

(22) Filed: Jan. 17, 2001

(65) Prior Publication Data

US 2001/0023304 A1 Sep. 20, 2001

(30) Foreign Application Priority Data

Jan. 18, 2000 (JP) ........................................ 2000-013904

(51) Int. Cl.$^7$ ............................................ C07C 229/00
(52) U.S. Cl. ........................................................ 560/1
(58) Field of Search ................ 562/565, 553, 562/561, 571

(56) References Cited

FOREIGN PATENT DOCUMENTS

| | | |
|---|---|---|
| EP | 0 853 986 A1 | 7/1998 |
| JP | 5-72695 | 3/1993 |
| JP | 6-67370 | 3/1994 |
| JP | 7-64260 | 3/1995 |
| JP | 7-89913 | 4/1995 |
| JP | 8-92197 | 4/1996 |
| JP | 8-165271 | 6/1996 |
| JP | 8-188549 | 7/1996 |
| JP | 9-87675 | 3/1997 |
| JP | 9-124567 | 5/1997 |
| RU | 316685 | 12/1971 |

OTHER PUBLICATIONS

Database WPI Section Ch, Week 199519, Derwent Publications Ltd., London, GB; Class E12, AN 1995–141889, XP002166220 & JP 07 064260 A (Fuji Photo Film Co., Ltd.), Mar. 10, 1995—abstract.

Misao Mashihara et al., "Synthesis and Metal Chelate Stability of N,N'–Ethylene–bis(aminomalonic) Acid", Bulletin of the Chemical Society of Japan, vol. 46, No. 3, Mar. 1973, pp. 844–847.

Bulletin of the Chemical Society of Japan, vol. 46, 844–847, 1973, Synthesis and Chelate stability of N,N'–Ethylenebis(aminomalonic) Acid, Masao Mashihara et al.

*Primary Examiner*—Johann Richter
*Assistant Examiner*—Paul A. Zucker
(74) *Attorney, Agent, or Firm*—Sughrue Mion, PLLC

(57) ABSTRACT

An aminopolycarboxylate is described, which is represented by the following formula (1):

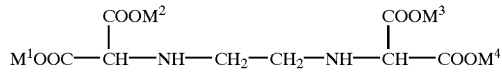

(1)

wherein $M^1$, $M^2$, $M^3$ and $M^4$ independently represent each an alkali metal ion. A process for producing the aminopolycarboxylate; a biodegradable chelating agent which comprises as the active component the aminopolycarboxylate; and a sequestering agent which comprises as the active component the aminopolycarboxylate are also described.

6 Claims, 1 Drawing Sheet

US 6,465,676 B2

AMINOPOLYCARBOXYLATES, PROCESS FOR PRODUCING THE SAME AND USE THEREOF

FIELD OF THE INVENTION

This invention relates to highly biodegradable aminopolycarboxylates which are useful as chelating agents, a process for producing the same and use thereof.

BACKGROUND OF THE INVENTION

As chelating agents for capturing metals contained in, for example, waste water, it has been a practice to employ electrolytic polymers such as polyacrylic acid and polymaleic acid, aminocarboxylates such as ethylenediaminetetraacetic acid (EDTA) and nitrilotriacetic acid, polyphosphates such as sodium tripolyphosphate. However, these conventional chelating agents are each poor in biodegradability. Therefore, it has been feared in recent years that they might exert undesirable effects on the environment.

Accordingly, there have been proposed various biodegradable chelating agents. JP-A-5-72695 discloses N,N'-alkylenediaminedisuccinic acids, JP-A-8-165271 discloses 2-hydroxy-1,3-propanediaminepolycarboxylic acids, JP-A-9-87675 discloses unsaturated aminocarboxylic acids, JP-A-9-124567 discloses 2,2'-dimethyliminodiacetic acid derivatives, JP-A-8-188549 discloses glycerol derivatives, JP-A-8-92197 discloses 2-sulfoethylaminocarboxylic acids, and JP-A-7-89913 discloses aspartic acid derivatives (The term "JP-A" as used herein means an "unexamined published Japanese patent application").

Moreover, JP-A-6-67370 and JP-A-7-64260 disclose ethylenediamine-N,N'-dimalonic acid and its iron (III) complex salt as components of solutions for processing silver halide photographic materials. It is also disclosed in these references that these compounds have biodegradability. It is stated in these references that ethylenediamine-N,N'-dimalonic acid was synthesized in accordance with Misao M. et al., Bull. Chem. Soc. Japan., vol. 46, pp. 844 to 847 (1973) (hereinafter referred to as the "document 1") or USSR Patent No. 316685. A production process starting with a malonic acid salt is disclosed in the document 1 or USSR Patent No. 316685. No process but the one described above has been known hitherto as a process for producing ethylenediamine-N,N'-dimalonic acid.

However these biodegradable chelating agents proposed so far are unsatisfactory in chelatability and chemical stability. To industrially use these chelating agents, it is therefore required to further improve the qualities thereof.

In case where ethylenediamine-N,N'-dimalonic acid is produced with the use of a malonic acid salt as a starting material in accordance with the process described in the document 1 or USSR Patent No. 316685, the resultant compound is liable to degrade and ethylenediamine-N,N'-diacetic acid is formed as a by-product by decarboxylation, thereby lowering the yield. Thus, this process is unsatisfactory from an industrial viewpoint.

It is stated in the document 1 that although disodium ethylenediamine-N,N'-dimalonate was produced, the product has only a poor chelatability due to the steric hindrance of the structure of this compound. It is also stated therein that a tetraalkali metal salt of ethylenediamine-N,N'-dimalonic acid is liable to be hydrolyzed. The document 1 presents neither any example of the isolation of the tetrasodium salt nor any example of the production thereof.

JP-A-7-64260 discloses use as a bleaching agent and neither the tetrasodium salt nor use thereof as a chelating agent is described therein. In this reference, the iron (III) complex salt of ethylenediamine-N,N'-dimalonic acid was synthesized in accordance with the document 1 and ethylenediamine-N,N'-dimalonic acid or disodium salt thereof was used as an intermediate in producing the iron (III) complex salt of ethylenediamine-N,N'-dimalonic acid.

SUMMARY OF THE INVENTION

The invention, which has been completed by taking the above-described problems into consideration, aims at providing chelating compounds, which are superior in chelatability and chemical stability to the chelating agents proposed hitherto and have high biodegradability, a process for producing the same and use thereof.

By considering the problems as described above, the inventors have paid attention particularly to the chelatability and biodegradability of aminocarboxylic acid chelating agents and conducted intensive studies. As a result, they have found out:

1) an aminopolycarboxylate represented by the following formula (1):

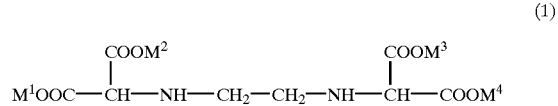

(1)

wherein $M^1$, $M^2$, $M^3$ and $M^4$ independently represent each an alkali metal ion has a high chelatability and an excellent biodegradability and the chemical stability can be extremely elevated by forming alkali metal salts of all of the four constituting carboxylic acids;

2) in producing this aminopolycarboxylate, the aminopolycarboxylate represented by the formula (1) can be obtained in a high purity and at a high yield by reacting ethylenediamine with a malonic acid ester derivative in a liquid containing alkali metal(s) and recrystallizing the alkali metal aminopolycarboxylate thus formed from a solvent mixture of water with a poor solvent compatible with water, or crystallizing by adding a poor solvent compatible with water to an aqueous solution of the alkali metal aminopolycarboxylate thus formed;

3) the highly pure aminopolycarboxylate obtained by this process is highly stable and undergoes substantially no degradation even under heating at 50° C.; and 4) this aminopolycarboxylate is excellent in the ability to capture metals contained in, for example, waste water. The invention has been completed on the basis of these findings.

Accordingly, the invention relates to aminopolycarboxylates represented by the formula (1) as described above, a process for producing the aminopolycarboxylates by reacting ethylenediamine with a malonic acid ester derivative, and use the aminopolycarboxylates such as chelating agents containing the same as the active component.

Figure 1:
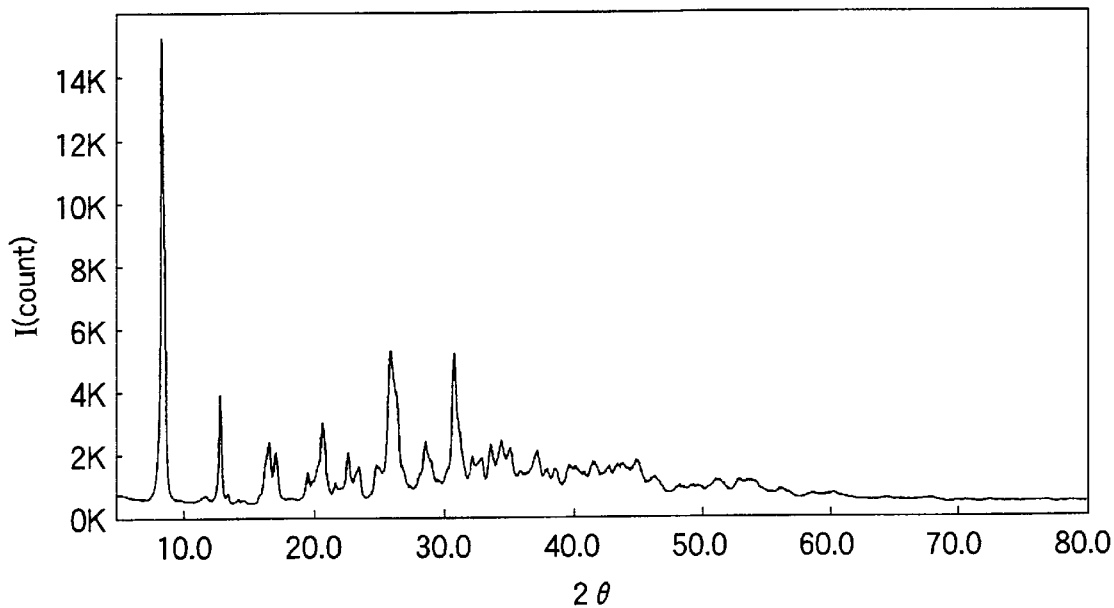
FIG. 1 shows the powdery X-ray diffraction pattern of the crystals obtained in Example 2 wherein the abscissa (X-axis) indicates the diffraction angle 2θ (expressed in deg) which is the diffraction angle in the X-ray diffractometry, while the ordinate (Y-axis) indicates the peak intensity in the X-ray diffractometry presented on an arbitrary scale.

indicates the diffraction angle 2θ (expressed in deg) which is the diffraction angle in the X-ray diffractometry, while the ordinate (Y-axis) indicates the peak intensity in the X-ray diffractometry presented on an arbitrary scale.

DETAILED DESCRIPTION OF THE INVENTION

Now, the invention will be described in greater detail.

Aminopolycarboxylate

The aminopolycarboxylates according to the invention mean compounds represented by the formula (1) and hydrates thereof are also involved.

In the formula (1), $M^1$, $M^2$, $M^3$ and $M^4$ represent each an alkali metal ion such as lithium ion, sodium ion, potassium ion, rubidium ion or cesium ion. Although each of these ions is usable, it is preferable in practice to use sodium ion and potassium ion which are less expensive. It is still preferable from an industrial viewpoint to use sodium ion therefor.

It is theoretically possible to introduce four kinds of ions into the four carboxylic acids in the formula (1). However, $M^1$, $M^2$, $M^3$ and $M^4$ may be the same ions. It is important herein that none of $M^1$, $M^2$, $M^3$ and $M^4$ substantially represents a hydrogen ion. In case either one of them is a hydrogen ion, the chemical stability of the aminopolycarboxylate is largely lowered. That is to say, the aminopolycarboxylate is liable to undergo decarboxylation, which makes it difficult to industrially employ this compound. Accordingly, it is important in the aminopolycarboxylate of the invention that the alkali metal ion(s) are present in an amount of at least 4.0 times by mol as much as the aminopolycarboxylic acid. Owing to this constitution, the aminopolycarboxylate becomes chemically stable.

It is favorable that the aminopolycarboxylate according to the invention has a high purity. The term a "high purity" as used herein usually means a purity of 90% or more, preferably 95% or more and still preferably 99% or more. When the purity of the aminopolycarboxylate is 95% or more, it becomes highly stable and undergoes no degradation even under heating at 50° C.

The aminopolycarboxylate according to the invention remains stable in the state of an aqueous solution. In this case, it is important that the alkali metal ion(s) are present, as a base, in an amount of at least 4.0 times by mol as much as the aminopolycarboxylic acid. When the amount of the alkali metal ion(s) is less than 4.0 times by mol based on the aminopolycarboxylic acid, a tetraalkali metal salt can be hardly formed as described above. In this case, the chemical stability is lowered and the compound degrades due to decarboxylation, which sometimes makes it hardly usable industrially.

The aminopolycarboxylate of the invention can be isolated in the form of crystals which are stable and easily handled industrially. When these stable crystals are measured by the powder X-ray diffractometry with the use of a CuKα ray, tetrasodium salt, among the aminopolycarboxylates of the invention, shows diffraction X-ray peaks at least at diffraction angles of 8.6°, 12.9°, 26.2°, 26.6° and 31.0°. On the other hand, tetrapotassium salt shows diffraction X-ray peaks at least at diffraction angles of 17.9°, 24.4°, 30.0° and 31.0°, though some errors caused by measurement errors arise therein.

The crystals of the aminopolycarboxylate according to the invention may be in the form of either a powder or granules. Namely, an appropriate form may be selected depending on the purpose of use.

Process for Producing Aminopolycarboxylate

The aminopolycarboxylate according to the invention can be obtained in a high purity and at a high yield by reacting one molecule of ethylenediamine with two molecules of a malonic acid ester derivative in a liquid containing alkali metal(s) and recrystallizing the alkali metal aminopolycarboxylate thus formed from a solvent mixture of water with a poor solvent compatible with water. Alternatively, it can be obtained in a high purity and at a high yield by crystallizing by adding a poor solvent compatible with water to an aqueous solution of the alkali metal aminopolycarboxylate formed in the same manner.

In the process according to the invention, it is first important to use not a malonic acid derivative but a malonic acid ester derivative. This is because, when a malonic acid derivative is used, the chemical stability of the product is extremely lowered, namely, the product is liable to be decarboxylated. As a result, the yield of the aminopolycarboxylate of the invention, which is obtained as the final product, is lowered.

In the process according to the invention, use may be made a malonic acid ester derivative having an elimination group in the methylene moiety of malonic acid. Examples of the elimination group include halogens and sulfonates. Halogens are preferable therefor because of the easiness in synthesis. Although halogenated malonic acid esters may be produced by an arbitrary method without restriction, malonic acid esters can be easily halogenated by, for example, a method described in Organic Syntheses, I. p. 245 (1941). Although the halogenation may be performed by using either fluorine, chlorine, bromine or iodine, it is preferable to use chlorine or bromine in the halogenation since these halogens can be easily handled.

In the process of the invention, the reaction between the malonic acid ester derivative and ethylenediamine can be carried out under heating. Alternatively, the reaction may be carried out at such a low temperature that the liquid reaction mixture is not solidified or at room temperature.

In the process of the invention, it is favorable that the malonic acid ester derivative is added in an amount twice to thrice by mol as much as ethylenediamine, though the amount is not restricted thereto. In case where the malonic acid ester derivative is added in an amount less than twice as much as ethylenediamine, a reaction intermediate wherein one malonic acid ester molecule is attached to ethylenediamine is sometimes formed and the reaction product is contaminated therewith. On the other hand, addition of the malonic acid ester derivative in an amount exceeding thrice as much as the ethylenediamine sometimes results in an industrial disadvantage.

Now, the production of the aminopolycarboxylate by the process according to the invention will be described. The ethylenediamine and the malonic acid ester derivative to be used may be added in an arbitrary manner without restriction. For example, the malonic acid ester derivative may be dropped into an aqueous alkali solution of ethylenediamine. Alternatively, ethylenediamine and the malonic acid ester derivative may be added simultaneously to an aqueous alkali solution.

In the process according to the invention, the reaction between the malonic acid ester derivative and ethylenediamine is performed in an aqueous alkali solution. In this reaction, the liquid reaction mixture has a pH value of 7 or higher, preferably from pH 8 to 14. As the alkali to be used in the reaction, use may be made of hydroxides (for example, sodium hydroxide, potassium hydroxide, lithium hydroxide), carbonates (for example, sodium carbonate, potassium carbonate, lithium carbonate), hydrogencarbonates (for example, sodium hydrogencarbonate, potassium hydrogencarbonate, lithium hydrogencarbonate), oxides (for example, sodium oxide, potassium oxide, lithium oxide), or metals (for example, metallic sodium, metallic potassium, metallic lithium) dissolved in water or materials which are soluble in water to give an alkaline solution. To capture the halogen formed in the course of the reaction and to hydrolyze the ester, the alkali is to be added at least in the equimolar amount to the malonic acid ester derivative, preferably 2 to 4 times by mol as much as the malonic acid ester derivative.

In the process according to the invention, it is secondly important that the aminopolycarboxylate, which has been formed by the reaction between the malonic acid ester derivative with ethylenediamine, is purified by crystallization or recrystallization. In case where the aminopolycarboxylate is purified by acidification, the dialkali metal aminopolycarboxylate is crystallized and thus the tetraalkali metal aminopolycarboxylate of the invention cannot be obtained. in addition, the dialkali metal salt undergoes degradation and thus the purity is lowered.

In case where crystallization is employed in the process of the invention, a poor solvent compatible with water (for example, an alcohol) is added to the aqueous solution of the aminopolycarboxylate. In case of employing recrystallization, it may be carried out in a solution wherein a poor solvent compatible with water (for example, an alcohol) is mixed with water.

Although the solvent to be used in these purification procedures in the process according to the invention is not restricted to alcohols but other water-compatible solvents may be used, it is industrially advantageous to use alcohols which are inexpensive. Examples of alcohols usable herein include methanol, ethanol, propanol, butanol, pentanol, hexanol, heptanol, cyclohexanol, ethylene glycol and glycerol. Among all, it is preferable to use methanol, ethanol and propanol which are highly compatible with water.

Use of Aminopolycarboxylate

The aminopolycarboxylates of the present invention thus obtained are usable as chelating agents. More particularly speaking, they are usable as sequestering agents because of showing chelatability on metals. As chelating agents, the aminopolycarboxylates may be employed alone. Alternatively, they may be combined with other agents. Although these other agents may be arbitrary ones without restriction so long as the effects of the invention are not worsened thereby, it is favorable that the chelating agents further contain alkali metal ions.

An aminopolycarboxylate degrades into ethylenediaminediacetic acid. The degradation of the aminopolycarboxylate is accompanied by the generation of acidic carbon dioxide gas. Carbon dioxide gas is present in the atmosphere too. This acidic carbon dioxide gas serves as a catalyst to thereby accelerate the degradation of the aminopolycarboxylate. In case where the content of the alkali metal salt is less than 4.0 times by mol (equivalent) as much as the aminopolycarboxylic acid, the catalytic action of the carbon dioxide gas cannot be inhibited. By adding alkali metal ion(s) in an amount of at least 4.0 times by mol (equivalent) as much as the aminopolycarboxylic acid, the catalytic action of the carbon dioxide gas can be inactivated and the degradation of the aminopolycarboxylate can be thus inhibited.

When the aminopolycarboxylates according to the invention are to be used as chelating agents, the particular method and dose thereof vary from purpose to purpose and, therefore, cannot be specified in general. As a rule, they may be used almost in the same manner as those commonly employed for each purpose. However, it is needless to say that the aminopolycarboxylates obtained by the process of the invention are expected as usable in novel cases and can achieve comparable effects to the conventional agents in a reduced dose, owing to the excellent functions and effects thereof.

The aminopolycarboxylates of the invention represented by the formula (1) can chelate metals in water as chelating agents (more particularly speaking, as sequestering agents). Owing to this ability, they are widely usable in, for example, fiber dyes, photographic chemicals, paper and pulp bleaching agents, soaps, detergent builders, scaling inhibitors, complexing agents for surface-treating metals and metal ion hiding agents for analytical use.

Further, the aminopolycarboxylates obtained by the process according to the invention are highly stable owing to the high purity and biodegradable, which makes it possible to reduce the load on the environment compared with the conventional chelating agents such as ethylenediaminetetraacetic acid.

By using the process according to the invention, the aminopolycarboxylates represented by the formula (1) can be obtained in a high purity and at a high yield.

According to the invention, the following effects can be achieved.

1) The aminopolycarboxylates of the invention have such a high biodegradability as not causing any environmental problem, an extremely high chelatability compared with the biodegradable chelating agents proposed hitherto, and an extremely high chemical stability.
2) The process of the invention makes it possible to produce the aminopolycarboxylates represented by the formula (1) in a high purity and at a high yield.
3) Because of having a high chelatability and an extremely high biodegradability, the agents of the invention are excellent from the viewpoint of environmental problems too.

Now, the invention will be described in greater detail by reference to the following Examples. However, it is to be understood that the invention is not construed as being limited thereto.

Production Example: Production of Diethyl Bromomalonate 16.0 g of diethyl malonate was added to 27.3 g of carbon tetrachloride. Into the resultant mixture was dropped 16.4 g of bromine under stirring at room temperature. After the completion of the dropping, the mixture was heated to 80° C. and refluxed for 1 hour to thereby remove hydrogen bromide formed by the reaction. The liquid reaction mixture thus obtained was washed with a 5% aqueous solution of sodium carbonate and carbon tetrachloride was distilled off. Then distillation was carried out to give 19.1 g (yield: 80.0%) of diethyl bromomalonate.

EXAMPLE 1

6.4 g of diethyl bromomalonate was dropped into a round-bottom glass flask containing 0.8 g of ethylenediamine, 3.5 g of sodium hydroxide and 15.0 g of water while stirring under ice-cooling over about 1 hour. At the completion of the dropping, the pH value was 12.8. The liquid reaction mixture was adjusted to pH 3.0 by adding dilute hydrochloric acid. As a result, white crystals were precipitated. After adding sodium hydroxide, these crystals were dissolved in water again and adjusted to pH 3.0 by adding dilute hydrochloric acid. Thus crystals having a purity of 97% were obtained. After adding sodium hydroxide, these crystals were dissolved in water and methanol was added thereto. Thus crystals of tetrasodium aminopolycarboxylate represented by the formula (1) were precipitated. The purity of these tetrasodium salt crystals was 99.6% and the yield on the basis of ethylenediamine was 75.2%.

Tetrasodium aminopolycarboxylate represented by the formula (1):

$^1$H-NMR:$CH_2$ ($\delta$ 2.60 ppm, s); CHCOO ($\delta$ 3.66 ppm, s); $^{13}$C-NMR:$CH_2$ ($\delta$ 50.8 ppm); CH ($\delta$ 74.7 ppm); COO ($\delta$ 182.1 ppm).

This tetrasodium aminopolycarboxylate was subjected to a chemical stability test by storing at 50° C. for 2 weeks. As a result, it showed no decrease in the purity.

To 1 mmol/l aqueous solution of this sodium aminopolycarboxylate, an equivalent amount of a 1 mmol/l aqueous solution of calcium chloride was added. Then the constant of calcium ion stability (pKCa$^{2+}$) was determined by measuring the calcium ion concentration at pH 10.0 by using a calcium ion electrode. As a result, the pKCa$^{2+}$ at 25° C. was 4.2.

Further, the sodium aminopolycarboxylate concentration was adjusted to 30 mg/l and 100 mg/l of activated sludge was added thereto. Then a biodegradability test was carried out at 25° C. for 2 weeks. As a result, 80% of the aminopolycarboxylic acid had been degraded.

EXAMPLE 2

Synthesis was carried out as in Example 1 and dilute hydrochloric acid was added to adjust the pH value to 3.0. The crystals thus precipitated had a purity of 90%. 3.0 g of these crystals were dissolved in 20 ml of a 1 mol/l aqueous solution of sodium hydroxide and methanol was added thereto. Thus, 2.8 g of white tetrasodium salt crystals were precipitated. These crystals had a purity of 99.3%. When measured by the powder X-ray diffractometry with the use of a CuK$\alpha$ ray, these crystals exhibited a crystal form as shown in FIG. 1.

EXAMPLE 3

31.8 g of diethyl bromomalonate was dropped into a round-bottom glass flask containing 4.0 g of ethylenediamine, 22.5 g of potassium hydroxide and 70.3 g of water while stirring under ice-cooling. The liquid reaction mixture was adjusted to pH 3.0 by adding dilute hydrochloric acid. As a result, white crystals were precipitated. After adding potassium hydroxide, these crystals were dissolved in water again and methanol was added thereto. Thus, white crystals of tetrapotassium salt were precipitated. The purity of this tetrapotassium salt crystals was 96.4% and the yield on the basis of ethylenediamine was 10.8%.

Figure 2:
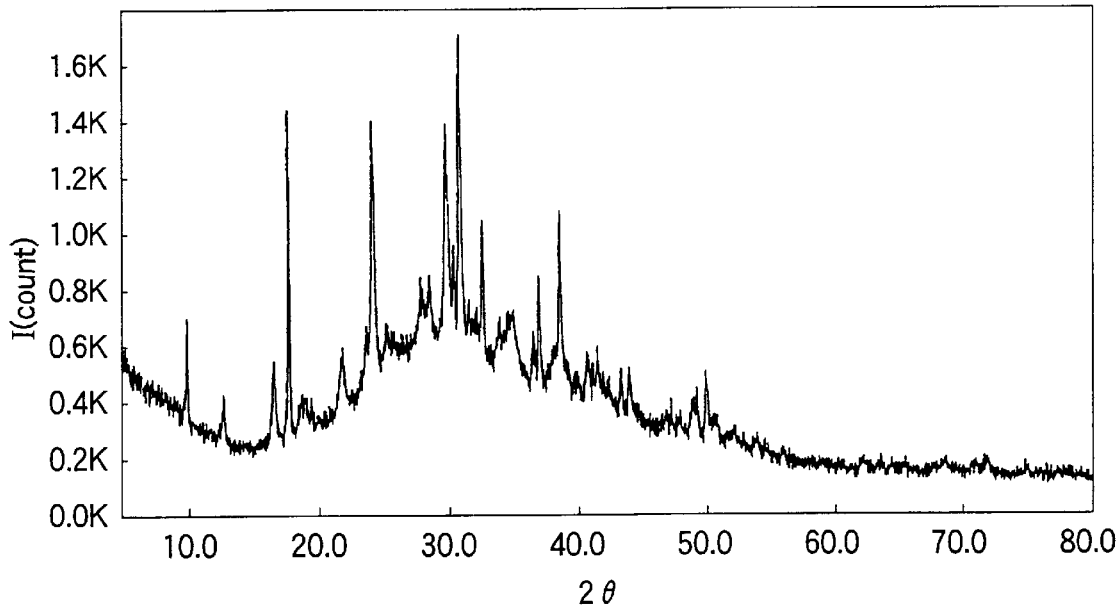
FIG. 2 shows the powdery X-ray diffraction pattern of the crystals obtained in Example 3 wherein the abscissa (X-axis)

This tetrapotassium aminopolycarboxylate was subjected to a chemical stability test by storing at 50° C. for 2 weeks. As a result, it showed no decrease in the purity. When measured by the powder X-ray diffractometry with the use of a CuK$\alpha$ ray, these crystals exhibited a crystal form as shown in FIG. 2.

COMPARATIVE EXAMPLE 1

The tetrasodium aminopolycarboxylate synthesized in Example 1 was dissolved in water and dilute hydrochloric acid was added thereto to give a disodium salt. This disodium salt was subjected to a chemical stability test by storing at 50° C. for 2 weeks. As a result, 85% of this compound had been degraded due to decarboxylation.

This result indicates that the disodium salt is inferior in the chemical stability to the tetrasodium salt.

COMPARATIVE EXAMPLE 2

To a 1 mmol/l aqueous solution of a marketed biodegradable chelating agent (trisodium N,N'-ethylenediaminedisuccinate), an equivalent amount of a 1 mmol/l aqueous solution of calcium chloride was added. The calcium ion concentration at pH 10 was measured with the use of a calcium ion electrode to determine the constant of calcium ion stability (pKCa$^{2+}$). As a result, the pKCa$^{2+}$ at 25° C. was 3.8. Further, the concentration of this trisodium N,N'-ethylenediaminedisuccinate was adjusted to 30 mg/l and 100 mg/l of activated sludge was added thereto. Then a biodegradability test was carried out at 25° C. for 4 weeks. As a result, 80% or more of the trisodium N,N'-ethylenediaminedisuccinate had been degraded.

These results indicate that trisodium N,N'-ethylenediaminedisuccinate is biodegradable but inferior in the chelatability to the tetrasodium aminopolycarboxylate.

COMPARATIVE EXAMPLE 3

To a 1 mmol/l aqueous solution of a marketed chelating agent (tetrasodium ethylene-diaminetetraacetate), an equivalent amount of a 1 mol/l aqueous solution of calcium chloride was added. The calcium ion concentration at pH 10 was measured with the use of a calcium ion electrode to determine the constant of calcium ion stability (pKCa$^{2+}$). As a result, the pKCa$^{2+}$ at 25° C. was 6.6. Further, this chelating agent was subjected to the biodegradability test as in Example 1. As a result, it had been scarcely degraded.

Thus, it is clarified that tetrasodium ethylenediaminetetraacetate has a chelatability but inferior in the biodegradability to the tetrasodium aminopolycarboxylate.

COMPARATIVE EXAMPLE 4

Aminopolycarboxylic acid was synthesized in accordance with the document 1. Namely, 9.2 g of bromomalonic acid and 30 ml of water were introduced into a three-necked glass flask (200 ml) and the pH value was adjusted to 7 by using a 30% aqueous solution of sodium hydroxide under cooling in an ice-bath. Then 1.5 g of ethylenediamine was slowly added to the aqueous solution which was maintained at 3 to 5° C. At this point, the pH value of the liquid reaction mixture was 11. After the completion of the addition of ethylenediamine, the liquid reaction mixture was slowly heated to 70° C. while adjusting the pH value within a range of 9 to 11 by using a 30% aqueous solution of sodium hydroxide. The liquid reaction mixture was heated to 70° C. for about 1 hour while maintaining the pH value within a range of 9 to 11 by using a 30% aqueous solution of sodium hydroxide. After the completion of the heating, it was cooled to room temperature. The pH value at this point was 10.3. Then the liquid reaction mixture was cooled in an ice-bath and dilute hydrochloric acid was dropped thereinto while maintaining the mixture at 5° C. or below. Thus, 2.2 g of yellow crystals were obtained. These yellow crystals were free from the tetrasodium salt but contained the disodium salt as the main component at a purity of 39%.

To a 1 mmol/l aqueous solution of the yellow crystals, an equivalent amount of a 1 mmol/l aqueous solution of calcium chloride was added. The calcium ion concentration at pH 10 was measured with the use of a calcium ion electrode to determine the constant of calcium ion stability ($pKCa^{2+}$). As a result, the $pKCa^{2+}$ at 25° C. was 3.2.

A comparison of Examples with Comparative Example 4 indicates that the tetrasodium salt was obtained in Examples but not in Comparative Example 4. In the chelatability test, the product of Comparative Example 4 was inferior in the chelatability to the products of Examples.

In the following Examples and Comparative Examples, various chelating agents were examined in chemical stability, heat stability and biodegradability. These properties were determined under the conditions as will be specified below.

Chelatability (Constant of Stability) Test
(1) Formation of Calibration Curve

By using calcium chloride, solutions having calcium concentrations of 0.1 mmol/l, 1.0 mmol/l and 10 mmol/l were prepared and the potential of each solution was measured. Based on the data thus obtained, a calibration curve of the logarithmic calcium ion concentration vs. potential was formed.

(2) Measurement of Constant of Stability

An aqueous solution (100 ml) was prepared by adding a chelating agent (1 mmol/l) and calcium chloride (1 mmol/l) at an equivalent ratio to an aqueous solution containing 0.1 mmol/l of ammonium chloride to achieve a constant ionic strength. After stirring this solution for 10 minutes, the potential of the solution at 25° C. at pH 10 was measured. Based on the calibration curve formed in (1), the calcium ion concentration corresponding to the potential thus measured was determined and the constant of stability was calculated on the assumption that the sample and calcium ion formed a complex at a ratio of 1:1.

Chemical Stability Test 10 g of each chelating agent was stored under a nitrogen atmosphere in a sealed state while continuously heating to 50° C.

After 2 weeks, it was analyzed by high performance liquid chromatography and the stability was determined based on the decrease in the chelating agent and the increase in the degradation products.

Biodegradability Test

The biodegradability of each test sample was measured under the following conditions in accordance with the modified MITI method specified in OECD Test Guideline.

| | |
|---|---|
| Sample concentration | 30 mg/l. |
| Activated sludge concentration | 100 mg/l. |
| Temperature | 25° C. ± 1° C. |
| Test period | 28 days. |
| Determination item | LC-MS (high performance liquid chromatography-mass spectrometer). |

EXAMPLE 4

6.4 g of diethyl bromomalonate produced in Production Example was dropped into a round-bottom glass flask containing 0.8 g of ethylenediamine, 3.5 g of sodium hydroxide and 15.0 g of water while stirring under ice-cooling over about 1 hour. At the completion of the dropping, the pH value was 12.8. By adding methanol to the liquid reaction mixture, white crystals of tetrasodium aminopolycarboxylate represented by the formula (1) were precipitated. These crystals had a purity of 99.6% and the yield was 75.2%. When measured by powdery X-ray diffractometry, these crystals exhibited a crystal form as shown in FIG. 1.

Tetrasodium aminopolycarboxylate represented by the formula (1):

$^1$H-NMR:$CH_2$ (δ 2.60 ppm, s); CHCOO (δ 3.66 ppm, s); $^{13}$C-NMR:$CH_2$ (δ 50.8 ppm); CH (δ 74.7 ppm); COO (δ 182.1 ppm).

The sodium content in this tetrasodium aminopolycarboxylate was determined by the water-dissolution-IC method. As a result, it contained 24% of sodium, namely, 4.2 mol of sodium per mol of aminopolycarboxylic acid.

Chemical Stability Test

This tetrasodium aminopolycarboxylate was subjected to the chemical stability test under continuously heating at 50° C. As a result, no increase in the degradation products was observed even after 2 weeks.

Measurement of Chelatability (Constant of Stability)

To 1 mmol/l aqueous solution of this tetrasodium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.2.

Biodegradability Test

This tetrasodium aminopolycarboxylate was subjected to the biodegradability test in accordance with the modified MITI method as specified in OECD Test Guideline 301C. Namely, the concentration of an aqueous solution of the tetrasodium aminopolycarboxylate was adjusted to 100 mg/l and 30 mg/l of activated sludge was added thereto. Then the biodegradability test was performed at 25° C. for 4 weeks. As a result, 80% or more of the tetrasodium aminopolycarboxylate had been degraded.

EXAMPLE 5

As in Example 4, 6.4 g of diethyl bromomalonate produced in Production Example was dropped into a reactor containing 0.8 g of ethylenediamine, 3.5 g of sodium hydroxide and 15.0 g of water while stirring under ice-cooling to thereby carry out the reaction. Methanol was slowly added to the liquid reaction mixture. When the precipitation of crystals began, the addition of methanol was ceased and the aqueous solution was stored in a refrigerator overnight to thereby accelerate the crystallization. After allowing to stand, the crystals thus precipitated were collected by filtration and dried under reduced pressure. Thus, white crystals of tetrasodium aminopolycarboxylate having a purity of 99.5% were obtained at a yield of 73.2%.

The sodium content in the obtained crystals was determined by the water-dissolution-IC method. As a result, the crystals contained 22% of sodium, namely, 4.1 mol of sodium per mol of aminopolycarboxylic acid.

Measurement of Chelatability (constant of stability)

To 1 mmol/l aqueous solution of this sodium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.2.

Biodegradability Test

This tetrasodium aminopolyearboxylate was subjected to the biodegradability test in accordance with the modified MITI method as specified in OECD Test Guideline 301C. Namely, the concentration of an aqueous solution of the tetrasodium aminopolycarboxylate was adjusted to 100 mg/l and 30 mg/l of activated sludge was added thereto. Then the biodegradability test was performed at 25° C. for 4 weeks. As a result, 80% or more of the tetrasodium aminopolycarboxylate had been degraded.

EXAMPLE 6

31.8 g of diethyl bromomalonate was dropped into a round-bottom glass flask containing 4.0 g of ethylenediamine, 22.5 g of potassium hydroxide and 70.3 g of water while stirring under ice-cooling. By adding methanol to the liquid reaction mixture, white crystals of tetrapotassium aminopolycarboxylate were precipitated. These tetrapotassium salt crystals had a purity of 96.4% and the yield was 10.8%.

The potassium content in this tetrapotassium aminopolycarboxylate was determined by the water-dissolution-IC method. As a result, it contained 34% of potassium, namely, 4.1 mol of potassium per mol of aminopolycarboxylic acid.

Chemical Stability Test

This tetrapotassium aminopolycarboxylate was subjected to the chemical stability test under heating at 50° C. As a result, no increase in the degradation products was observed even after 2 weeks. When measured by powdery X-ray diffractometry, these crystals exhibited a crystal form as shown in FIG. 2.

Measurement of Chelatability (Constant of Stability)

To 1 mmol/l aqueous solution of this tetrapotassium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.2.

Biodegradability Test

This tetrapotassium aminopolycarboxylate was subjected to the biodegradability test in accordance with the modified MITI method as specified in OECD Test Guideline 301C. Namely, the concentration of an aqueous solution of the tetrapotassium aminopolycarboxylate was adjusted to 100 mg/l and 30 mg/l of activated sludge was added thereto. Then the biodegradability test was performed at 25° C. for 4 weeks. As a result, 80% or more of the tetrapotassium aminopolycarboxylate had been degraded.

EXAMPLE 7

Tetrasodium aminopolycarboxylate was synthesized as in Example 4. The sodium content in this tetrasodium aminopolycarboxylate was determined by the water-dissolution-IC method. As a result, it contained 22% of sodium, namely, 4.0 mol of sodium per mol of aminocarboxylic acid. To this tetrasodium aminopolycarboxylate, 0.5 mol of sodium hydroxide was further added to give a chelating agent containing the alkali metal ion in excess.

Chemical Stability Test

When the chelating agent was subjected to the chemical stability test under continuously heating at 50° C., no increase in the degradation products was observed even after 2 weeks.

EXAMPLE 8

Tetrasodium aminopolycarboxylate crystals having a purity of 92.0% were obtained by performing the reaction as in Example 4. The sodium content in these crystals was determined by the water-dissolution-IC method. As a result, the crystals contained 22% of sodium, namely, 4.1 mol of sodium per mol of aminopolycarboxylic acid.

Chemical Stability Test

When the tetrasodium aminopolycarboxylate was subjected to the chemical stability test under heating at 50° C., it suffered from degradation at a ratio of 2.1% after 2 weeks.

Measurement of Chelatability (Constant of Stability)

To 1 mmol/l aqueous solution of this tetrasodium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.1.

Biodegradability Test

This tetrasodium aminopolycarboxylate was subjected to the biodegradability test in accordance with the modified MITI method as specified in OECD Test Guideline 301C. Namely, the concentration of an aqueous solution of the tetrasodium aminopolycarboxylate was adjusted to 100 mg/l and 30 mg/l of activated sludge was added thereto. Then the biodegradability test was performed at 25° C. for 4 weeks. As a result, 80% or more of the tetrasodium aminopolycarboxylate had been degraded.

COMPARATIVE EXAMPLE 5

6.4 g of diethyl bromomalonate obtained in Production Example was dropped into a round-bottom glass flask containing 0.8 g of ethylenediamine, 3.5 g of sodium hydroxide and 15.0 g of water while stirring under ice-cooling. By adding dilute hydrochloric acid to the liquid reaction mixture so as to adjust the pH value to 3.0, white crystals of sodium aminopolycarboxylate were precipitated.

The sodium content in this sodium aminopolycarboxylate was determined by the water-dissolution-IC method. As a result, it contained 12% of sodium, namely, 2.1 mol of sodium per mol of aminopolycarboxylic acid.

Chemical Stability Test

When this disodium salt was subjected to the chemical stability test under continuously heating at 50° C., 85% of the salt had been degraded due to decarboxylation after 2 weeks. <Measurement of Chelatability (Constant of Stability)

To 1 mmol/l aqueous solution of this disodium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.2.

Biodegradability Test

This disodium aminopolycarboxylate was subjected to the biodegradability test in accordance with the modified MITI method as specified in OECD Test Guideline 301C. Namely, the concentration of an aqueous solution of the disodium aminopolycarboxylate was adjusted to 100 mg/l and 30 mg/l of activated sludge was added thereto. Then the biodegradability test was performed at 25° C. for 4 weeks. As a result, 80% or more of the disodium aminopolycarboxylate had been degraded.

COMPARATIVE EXAMPLE 6

6.4 g of diethyl bromomalonate obtained in Production Example was dropped into a round-bottom glass flask containing 0.8 g of ethylenediamine, 4.9 g of potassium hydroxide and 15.0 g of water while stirring under ice-cooling. By adding dilute hydrochloric acid to the liquid reaction mixture so as to adjust the pH value to 3.0, white crystals of potassium aminopolycarboxylate were precipitated.

The potassium content in this potassium aminopolycarboxylate was determined by the water-dissolution-IC method. As a result, it contained 25% of potassium, namely, 2.2 mol of potassium per mol of aminocarboxylic acid. When this dipotassium salt was subjected to the chemical stability test under continuously heating at 50° C., 83% of the salt had been degraded due to decarboxylation after 2 weeks.

Measurement of Chelatability (Constant of Stability)

To 1 mmol/l aqueous solution of this dipotassium aminopolycarboxylate, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 4.2.

Biodegradability Test

This dipotassium aminopolycarboxylate was subjected to the biodegradability test in accordance with the modified MITI method as specified in OECD Test Guideline 301C. Namely, the concentration of an aqueous solution of the dipotassium aminopolycarboxylate was adjusted to 100 mg/l and 30 mg/l of activated sludge was added thereto. Then the biodegradability test was performed at 25° C. for 4 weeks. As a result, 80% or more of the dipotassium aminopolycarboxylate had been degraded.

COMPARATIVE EXAMPLE 7

Aminopolycarboxylic acid was synthesized in accordance with Bull. Chem. Soc. Japan., 46, 844 (1973). Namely, 9.2 g of bromomalonic acid and 30 ml of water were introduced into a three-necked glass flask (200 ml) and the pH value was adjusted to 7 by using a 30% aqueous solution of sodium hydroxide under cooling in an ice-bath. Then 1.5 g of ethylenediamine was slowly added to the aqueous solution which was maintained at 3 to 5° C. At this point, the pH value of the liquid reaction mixture was 11. After the completion of the addition of ethylenediamine, the liquid reaction mixture was slowly heated to 70° C. while adjusting the pH value within a range of 9 to 11 by using a 30% aqueous solution of sodium hydroxide. The liquid reaction mixture was heated at 70° C. for about 1 hour while maintaining the pH value within a range of 9 to 11 by using a 30% aqueous solution of sodium hydroxide. After the completion of the heating, it was cooled to room temperature. The pH value at this point was 10.3. Then the liquid reaction mixture was cooled in an ice-bath and dilute hydrochloric acid was dropped thereinto while maintaining the mixture to 5° C. or below. Thus, 2.2 g of yellow crystals were obtained. These yellow crystals were free from the tetrasodium salt but composed of the disodium salt with ethylenediaminediacetic acid. When the purity was measured, the disodium aminopolycarboxylate showed a purity of 39%.

Measurement of Chelatability (Constant of Stability)

To 1 mmol/l aqueous solution of these yellow crystals, an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 3.2.

Chemical Stability Test

When these crystals were subjected to the chemical stability test under continuously heating at 50° C., the crystals had been completely degraded within 2 weeks.

COMPARATIVE EXAMPLE 8

Measurement of Chelatability (Constant of Stability)

To 1 mmol/l aqueous solution of a marketed biodegradable chelating agent (trisodium N,N'-ethylenediaminedisuccinate), an equivalent amount of a 1 mmol/l aqueous solution of calcium chloride was added. Then the constant of calcium ion stability ($pKCa^{2+}$) was determined by measuring the calcium ion concentration at pH 10.0 by using a calcium ion electrode. As a result, the $pKCa^{2+}$ at 25° C. was 3.8.

Biodegradability Test

This trisodium N,N'-ethylenediaminedisuccinate was subjected to the biodegradability test in accordance with the modified MITI method as specified in OECD Test Guideline 301C. Namely, the concentration of an aqueous solution of the trisodium N,N'-ethylenediaminedisuccinate was adjusted to 100 mg/l and 30 mg/l of activated sludge was added thereto. Then the biodegradability test was performed at 25° C. for 4 weeks. As a result, 80% or more of the trisodium N,N'-ethylenediaminedisuccinate had been degraded.

COMPARATIVE EXAMPLE 9

Measurement of Chelatability (Constant of Stability)

To 1 mmol/l aqueous solution of a marketed chelating agent (tetrasodium ethylenediaminetetraacetate), an equivalent amount of a 1 mmol/l aqueous solution of calcium chloride was added. Then the constant of calcium ion stability (pKCa$^{2+}$) was determined by measuring the calcium ion concentration at pH 10. 0 by using a calcium ion electrode. As a result, the pKCa$^{2+}$ at 25° C. was 6.6.

Biodegradability Test

This chelating agent was subjected to the biodegradability test in accordance with the modified MITI method as specified in OECD Test Guideline 301C. As a result, the chelating agent had been scarcely degraded.

EXAMPLE 9

Tetrasodium aminopolycarboxylate crystals having a purity of 99.6% were obtained by the reaction as in Example 4. These tetrasodium aminopolycarboxylate crystals were dissolved in water to give a concentration of 10 mmol/l.

Chemical Stability Test

This aqueous solution of sodium aminopolycarboxylate was subjected to the chemical stability test under heating at 50° C. As a result, no increase in the degradation products was observed even after 2 weeks.

Measurement of Chelatability (Constant of Stability)

To 10 ml of 10 mmol/l aqueous solution of this sodium aminopolycarboxylate, 10 ml of a 10 mmol/l aqueous solution of calcium chloride was added and to the mixed solution was added aqueous solution of ammonium chloride to give a total volume of 100 ml, whereby an ionic strength was adjusted to 0.1 mol/l which was the same as that of a solid. Then the constant of calcium ion stability (pKCa$^{2+}$) was determined by measuring the calcium ion concentration at pH 10.0 by using a calcium ion electrode. As a result, the pKCa$^{2+}$ at 25° C. was 4.2.

COMPARATIVE EXAMPLE 10

Tetrasodium aminopolycarboxylate crystals obtained as in Example 4 were dissolved in water. Then hydrochloric acid in an equivalent amount to the aminopolycarboxylic acid was added to neutralize the solution. The aqueous solution was subjected to the chemical stability test under heating at 50° C. As a result, about 25% of the sodium aminopolycaroxylate had been degraded due to decarboxylation after 2 weeks.

While the invention has been described in detail and with reference to specific embodiments thereof, it will be apparent to one skilled in the art that various changes and modifications can be made therein without departing from the spirit and scope thereof.

What is claimed is:

1. A crystal of an aminopolycarboxylate represented by the following formula (1):

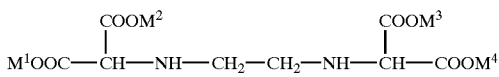

(1)

wherein M$^1$, M$^2$, M$^3$ and M$^4$ each represent a sodium ion and the crystal has a powder X-ray diffraction pattern with the use of a CuKα ray as shown in FIG. 1.

2. The crystal of an aminopolycarboxylate as claimed in claim 1, wherein said sodium ion is present in an amount of at least 4.0 times by mol as much as an aminopolycarboxylic acid.

3. The crystal of an aminopolycarboxylate as claimed in claim 1, wherein said crystal of an aminopolycarboxylate is in the form of a powder or granules.

4. A crystal of an aminopolycarboxylate represented by the following formula (1):

(1)

wherein M$^1$, M$^2$, M$^3$ and M$^4$ each represent a potassium ion and the crystal has a powder X-ray diffraction pattern with the use of CuKα ray as shown in FIG. 2.

5. The crystal of an aminopolycarboxylate as claimed in claim 4, wherein said potassium ion is present in an amount of at least 4.0 times by mol as much as an aminopolycarboxylic acid.

6. The crystal of an aminopolycarboxylate as claimed in claim 4, wherein said crystal of an aminopolycarboxylate is in the form of a powder or granules.

* * * * *